United States Patent
Ueno et al.

(10) Patent No.: US 10,788,472 B2
(45) Date of Patent: Sep. 29, 2020

(54) METHOD FOR EVALUATING THE QUALITY OF STEAM-TREATED PRODUCTS

(71) Applicant: NIPPON STEEL NISSHIN CO., LTD., Tokyo (JP)

(72) Inventors: Shin Ueno, Tokyo (JP); Tadashi Nakano, Tokyo (JP)

(73) Assignee: NIPPON STEEL NISSHIN CO., LTD., Tokyo (JP)

(*) Notice: Subject to any disclaimer, the term of this patent is extended or adjusted under 35 U.S.C. 154(b) by 0 days.

(21) Appl. No.: 16/499,331

(22) PCT Filed: Mar. 1, 2018

(86) PCT No.: PCT/JP2018/007758
§ 371 (c)(1),
(2) Date: Sep. 30, 2019

(87) PCT Pub. No.: WO2018/180169
PCT Pub. Date: Oct. 4, 2018

(65) Prior Publication Data
US 2020/0057038 A1    Feb. 20, 2020

(30) Foreign Application Priority Data
Mar. 31, 2017   (JP) ................. 2017-072420

(51) Int. Cl.
*G01N 33/00*   (2006.01)
*C23C 8/18*    (2006.01)

(52) U.S. Cl.
CPC ........... *G01N 33/0004* (2013.01); *C23C 8/18* (2013.01)

(58) Field of Classification Search
None
See application file for complete search history.

(56) References Cited

U.S. PATENT DOCUMENTS 4,348,886 A * 9/1982 Faith, Jr. .............. G01N 27/041
                                                             118/712
9,598,773 B2   3/2017 Nakano et al.
(Continued)

FOREIGN PATENT DOCUMENTS

CN    101133300 A    2/2008
CN    101769835 A    7/2010
(Continued)

OTHER PUBLICATIONS

European Patent Office, extended European search report dated Feb. 6, 2020, regarding European Patent Application No. 18776350.3.
(Continued)

*Primary Examiner* — Daniel S Larkin
(74) *Attorney, Agent, or Firm* — Li & Cai Intellectual Property (USA) Office

(57) ABSTRACT

The present invention provides a method for evaluating the quality of steam-treated products, allowing easy, quick and precise evaluation of the quality of oxide films in steam-treated products such as black coated steel sheets. Specifically, the present invention provides a method for evaluating the quality of steam-treated products with a surface oxide film formed during steam treatment, wherein test pieces (100) are cut out from said steam-treated products to measure the amount of oxygen in said test pieces (100) as a basis for evaluating the brightness of the surface(s) of said test pieces and/or the thickness of the oxide film of said test pieces.

2 Claims, 5 Drawing Sheets

(56) References Cited

U.S. PATENT DOCUMENTS

| | | |
|---|---|---|
| 2010/0098939 A1 | 4/2010 | Tada et al. |
| 2011/0186131 A1 | 8/2011 | Mukai et al. |
| 2015/0083276 A1 | 3/2015 | Nakano et al. |
| 2015/0336216 A1 | 11/2015 | Hattori et al. |
| 2017/0312860 A1 | 11/2017 | Hattori et al. |
| 2019/0062889 A1 | 2/2019 | Nakano et al. |

FOREIGN PATENT DOCUMENTS

| | | | |
|---|---|---|---|
| CN | 104246014 | A | 12/2014 |
| JP | 8213440 | A | 8/1996 |
| JP | 201282511 | A | 4/2012 |
| JP | 201282512 | A | 4/2012 |
| JP | 5335159 | B1 | 11/2013 |
| JP | 2014-095654 | A | 5/2014 |
| JP | 6072952 | B1 | 2/2017 |
| WO | WO2013161268 | A1 | 10/2013 |
| WO | WO201409052 | A1 | 7/2014 |
| WO | WO2014106013 | A1 | 7/2014 |
| WO | WO201671971 | A1 | 5/2016 |

OTHER PUBLICATIONS

Cho Lawrence, et al., "Surface Selective Oxidation of Sn-Added CMnSi TRIP Steel", Metallurgical and Materials Science, ASM International, Material Park, OH, US, vol. 47, No. 4, Jan. 19, 2016, pp. 1705-1719.
China Patent Office, Office Action dated Apr. 20, 2020, for Chinese Patent Application No. 201880021629.0.

* cited by examiner

| (a) | | | (b) | | |
|---|---|---|---|---|---|
| Surface brightness | Oxygen content | Oxide film thickness | Surface brightness | Oxygen content | Oxide film thickness |
| $\gamma_1$ | $\alpha_1$ | $\beta_1$ | $\gamma_2$ | $\alpha_2$ | $\beta_2$ |

| (c) | | | (d) | | |
|---|---|---|---|---|---|
| Surface brightness | Oxygen content | Oxide film thickness | Surface brightness | Oxygen content | Oxide film thickness |
| $\gamma_3$ | $\alpha_3$ | $\beta_3$ | $\gamma_4$ | $\alpha_4$ | $\beta_4$ |

| (e) | | |
|---|---|---|
| Surface brightness | Oxygen content | Oxide film thickness |
| $\gamma_5$ | $\alpha_5$ | $\beta_5$ |

FIG.5

METHOD FOR EVALUATING THE QUALITY OF STEAM-TREATED PRODUCTS

FIELD OF THE DISCLOSURE

The present invention relates to a method for evaluating the quality of steam-treated products, for example, products manufactured by treating coated steel sheets with steam.

BACKGROUND OF THE DISCLOSURE

The need for black steel sheets is increasing with design awareness in a number of fields, including roofing and exterior materials for buildings, home appliances and automobiles. The surface of steel sheets can be blackened by applying black paint to the surface and forming a black paint film thereon. The surface of steel sheets can also be blackened without forming a black paint film, specifically, by blackening the coating layer itself through oxidation, blocking the metallic gloss and silver-white tone of the coated steel sheets. For example, in patent documents 1 and 2, zinc-aluminum-magnesium (Zn—Al—Mg) alloy coated steel sheets have contact with steam in a closed container to form a black oxide film in the Zn—Al—Mg alloy coating layer.

In this specification, the treatment, in which treatment objects such as coated steel sheets have contact with steam in a closed container to blacken the coating layer, may be referred to as "steam treatment."

The coating layer, if oxidized to an inappropriate degree, may cause the following problems: the coating layer is insufficiently oxidized, and the brightness of the coating layer surface is excessively high, not allowing a good black appearance; the coating layer is excessively oxidized, and the oxide film is excessively thick, leading to embrittlement of the coating layer; the embrittlement of the coating layer reduces the corrosion resistance thereof, and bending the coated steel sheet causes the oxide film to come off and thus scatters powder; while bending the black coated steel sheet, the powder attaches to the mold and damages the oxide film surface or reduces formability. To ensure good quality of black coated steel sheets, the requirement is to evaluate the brightness of the coating layer surface and the thickness of the oxide film of black coated steel sheets and feed back the evaluation to the manufacturing process of black coated steel sheets (steam treatment of the coating layer) for quality control. Thus, standards were established to evaluate the brightness of the coating layer surface and the thickness of the oxide film in the coating layer.

Conventionally, brightness (L* value) of the coating layer surface has been measured using a spectral colorimeter to compare the measurement results with a brightness standard and thus evaluate the surface brightness.

Meanwhile, the thickness of the oxide film has been evaluated as follows: test pieces are cut out from the black coated steel sheet. The test pieces are embedded in liquid epoxy resin. After the epoxy resin hardens, the epoxy resin and the test pieces are flatly polished to expose the end faces of the test pieces. The end faces of the test pieces are observed with a microscope to measure the thickness of the oxide film. The average thickness of the oxide film is compared with a thickness standard to evaluate the thickness of the oxide film.

CITATION LIST

Patent Literature

Patent document 1 Japanese Patent No. 5335159
Patent document 2 Japanese Patent No. 6072952

SUMMARY OF THE DISCLOSURE

Technical Problem

The above-mentioned methods for evaluating oxide film thickness and surface brightness have the following problems: The method for evaluating oxide film thickness requires a cumbersome procedure, including embedding the test pieces in liquid epoxy resin, subsequent hardening, polishing the epoxy resin and the test pieces, and observation with a microscope. The hardening of liquid epoxy resin takes a long time, and the evaluation requires two or more days. Besides, the observation is limited to the end faces of test pieces, making it difficult to widely evaluate and average the thickness of the oxide film with high precision. Meanwhile, the method for evaluating surface brightness requires a spectral colorimeter that is not used in the method for evaluating oxide film thickness. Therefore, work efficiency is low when evaluating both oxide film thickness and surface brightness.

The present invention provides a method for evaluating the quality of steam-treated products, allowing easy, quick and precise evaluation of the quality of oxide films in steam-treated products such as black coated steel sheets.

Solution to Problem (1) The present invention provides a method for evaluating the quality of steam-treated products with a surface oxide film formed during steam treatment, wherein test pieces are cut out from said steam-treated products to measure the amount of oxygen in said test pieces as a basis for evaluating the brightness of the surface(s) of said test pieces and/or the thickness of the oxide film of said test pieces.

The inventors reached the idea of (1) as follows: To solve the above-described problems, the inventors studied the relationship between the amount of oxygen in steam-treated products with a surface oxide film formed during steam treatment (hereafter referred to as "steam-treated products") and the thickness of the oxide film of those steam-treated products. FIG. 3 shows the relationship between the amount of oxygen in test pieces from steam-treated products (hereafter occasionally referred to as "oxygen content"), indicated by the vertical axis, and the average thickness of the oxide film in those test pieces, indicated by the horizontal axis. As shown in FIG. 3, the oxygen content tends to increase as the average thickness of the oxide film (hereafter referred to as "oxide film thickness") increases. In FIG. 3, oxide film thickness and oxygen content are in one-to-one correspondence. Thus, the inventors found a definite correlation between oxygen film thickness and oxygen content.

The inventors further studied the relationship between oxide film thickness and brightness of the surface of steam-treated products (hereafter referred to as "surface brightness"). FIG. 4 shows the relationship between oxide film thickness, indicated by the horizontal axis, and surface brightness, indicated by the vertical axis. As shown in FIG. 4, surface brightness tends to decrease as oxide film thickness increases. In FIG. 4, oxide film thickness and surface brightness are in one-to-one correspondence. From FIGS. 3 and 4, it follows that surface brightness tends to decrease as oxygen content increases, and that oxygen content and surface brightness are in one-to-one correspondence. Thus, the inventors found a definite correlation between oxygen content and surface brightness.

Finding a definite correlation between oxygen content and oxide film thickness and a definite correlation between oxygen content and surface brightness, the inventors reached the idea of (1).

In construction (1), the amount of oxygen in test pieces (oxygen content) is measured as a basis for evaluating surface brightness and/or oxide film thickness. The measurement of oxygen content is easy and quick when compared to the conventional cumbersome procedure including embedding of test pieces in liquid epoxy resin, subsequent hardening, polishing the epoxy resin and the test pieces, and observation with a microscope. The evaluation of oxide film thickness based on oxygen content is wide-reaching and precise when compared to the conventional evaluation of oxide film thickness by merely observing the end faces of test pieces. In addition, the measurement of oxygen content allows evaluating both surface brightness and oxide film thickness. Therefore, work efficiency is high when compared to the conventional evaluation of surface brightness and oxide film thickness using a spectral colorimeter for surface brightness and a microscope for oxide film thickness.

(2) The present invention provides the method for evaluating the quality of steam-treated products according to (1), wherein said steam-treated products include a steel sheet and a coating layer (coating layers) integrally formed on the surface(s) of said steel sheet, said test pieces include a steel sheet cut-out part that is cut out from said steel sheets and a coating layer cut-out part (coating layer cut-out parts) integrally formed on the surface(s) of said steel sheet cut-out part, and said measurement of the amount of oxygen is performed by sending the test pieces integrating said steel sheet cut-out part and said coating layer cut-out part(s) to an oxygen amount measuring device.

In construction (2), the amount of oxygen is measured by sending the test pieces integrating a steel sheet cut-out part and a coating layer cut-out part (coating layer cut-out parts) to an oxygen amount measuring device. Because the coating layer cut-out part(s) is not separated from the steel sheet cut-out part, the amount of oxygen is easily and quickly measured.

Advantageous Effects of Invention

The present invention allows easy, quick and precise evaluation of the quality of oxide films in steam-treated products such as black coated steel sheets.

BRIEF DESCRIPTION OF THE DRAWINGS

FIG. 5 schematically shows the cross-sections of five test pieces in (a) to (e) with their measurement data on oxygen content, oxide film thickness and surface lightness.

DETAILED DESCRIPTION OF THE EXEMPLARY EMBODIMENTS

Below is a description of the manufacturing of black coated steel sheets, an example of steam-treated products according to the present invention, by treating Zn—Al—Mg alloy coated steel sheets with steam.

In this specification, Zn—Al—Mg alloy coated steel sheets may be referred to as "coated steel sheets," and the Zn—Al—Mg alloy coating layer as "the coating layer." In addition, the treatment, in which Zn—Al—Mg alloy coated steel sheets have contact with steam in a closed container to blacken the Zn—Al—Mg alloy coating layer, may be referred to as "steam treatment."

Method for Evaluating the Quality of Black Coated Steel Sheets

Black coated steel sheets, an example of steam-treated products according to the present invention, are manufactured by bringing Zn—Al—Mg alloy coated steel sheets into contact with steam in a closed container (steam treatment). Through the steam treatment, black coated steel sheets have an oxide film (a blackened coating layer).

The black coated steel sheets that will be subjected to the quality evaluation may, for example, comprise a substrate steel sheet and a coating layer integrally formed on one surface of the substrate steel sheet, or a substrate steel sheet and coating layers integrally formed on both surfaces of the substrate steel sheet.

Figure 1:
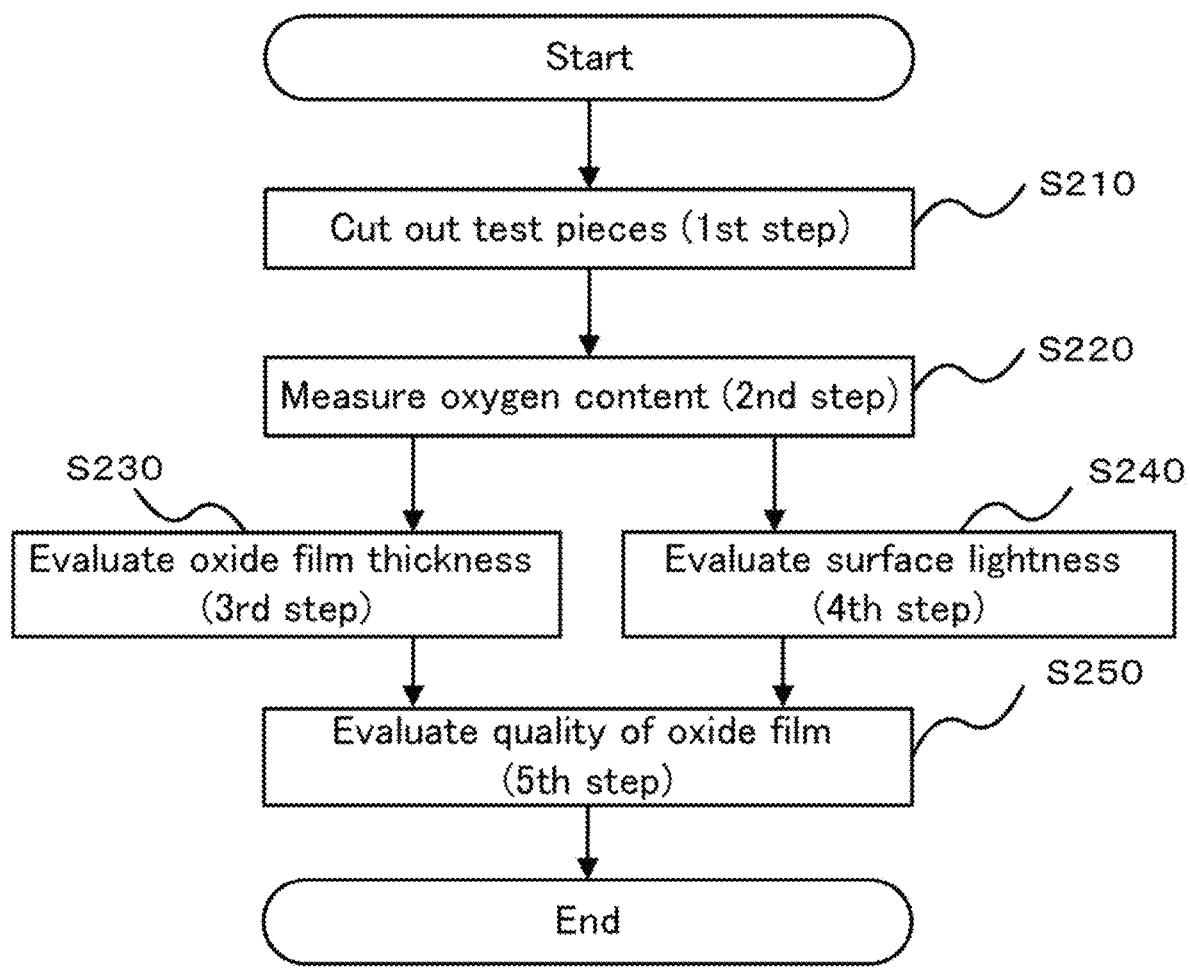
FIG. 1 is a flow chart of the method for evaluating the quality of black coated steel sheets according to the present invention.

As shown in the flow chart in FIG. 1, the method for evaluating the quality of black coated steel sheets according to the present invention involves five steps: first step (S210)—cutting out test pieces from the black coated steel sheet; second step (S220)—measuring the amount of oxygen in the test pieces; third step (S230)—evaluating the thickness of the oxide film of the black coated steel sheet based on the measured amount of oxygen; fourth step (S240)—evaluating the brightness of the surface of the black coated steel sheet based on the measured amount of oxygen; and fifth step (S250)—comprehensively evaluating the quality of the oxide film based on the evaluations in the third and fourth steps.

Below is a detailed description of the five steps.

(First Step)

The first step (S210) cuts out test pieces (100) (samples) from the black coated steel sheet (see FIG. 5).

Figure 2:
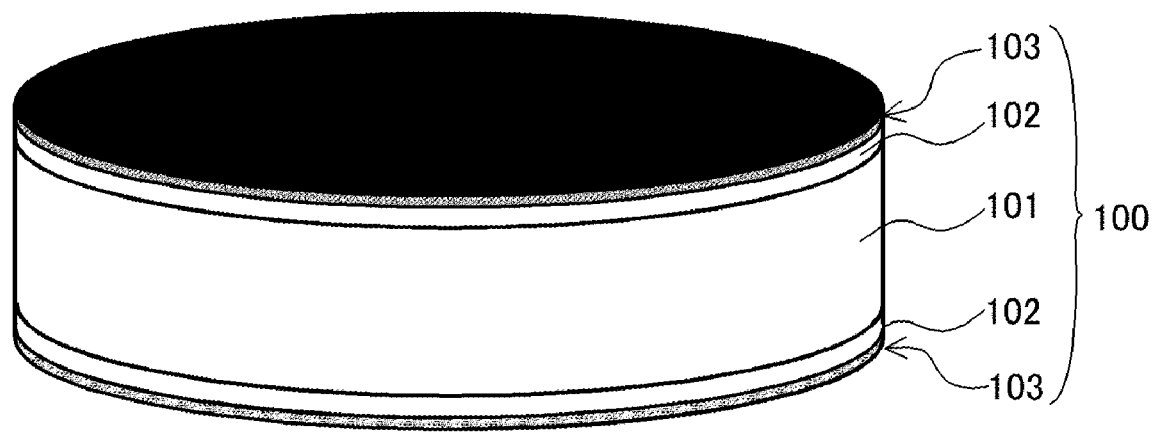
FIG. 2 is a perspective view of an example of a test piece.

The test pieces (100) are cut out from the black coated steel sheet, for example, by stamping out a predefined form using a mold (a punch or die). The form or size of the test pieces (100) has no special restrictions. For example, test pieces (100) can be discs with a diameter of 8 mm. The test pieces (100) can also have other forms. The test pieces (100) include a steel sheet cut-out part (101) that is cut out from the black coated steel sheet, and a coating layer cut-out part (coating layer cut-out parts) (102) that is cut out from the coating layer of the black coated steel sheet, integrally formed on the surface(s) of the steel sheet cut-out part (101) (see FIG. 2). The example in FIG. 2 shows the test piece (100) having a steel sheet cut-out part (101) and coating layer cut-out parts (102) on both surfaces of the steel sheet cut-out part (101). There is an oxide film (103) on the surface of the coating layer cut-out parts (102).

(Second Step)

The second step (S220) measures the amount of oxygen in the test pieces (100).

The amount of oxygen can be measured using an oxygen amount measuring device that allows precise measurement. The oxygen amount measuring device can be a well-known device. One example is an oxygen amount measuring device that comprises an analytical furnace with a graphite crucible for inserting test pieces, a gas cylinder for supplying inert gas such as helium (He) to the analytical furnace, and an infrared gas analyzer for analyzing the gas passing the analytical furnace and thus measuring the amount of oxygen in test pieces. For example, the infrared gas analyzer can be a non-dispersive infrared (NDIR) gas analyzer or a Fourier transform infrared (FTIR) gas analyzer. Other devices are possible if they can measure the precise amount of oxygen.

In the oxygen amount measuring device described above, the test pieces (100) and metal solvent are introduced into the graphite crucible. Receiving a supply of inert gas from the gas cylinder, the analytic furnace heats and melts the test pieces (100). The melting of the test pieces (100) generates carbon monoxide and carbon dioxide, which are analyzed by an infrared gas analyzer to measure the amount of oxygen in the test pieces (100). For example, tin (Sn) pellets or nickel (Ni) pellets can be used as the metal solvent mentioned above.

(Third Step)

Figure 3:
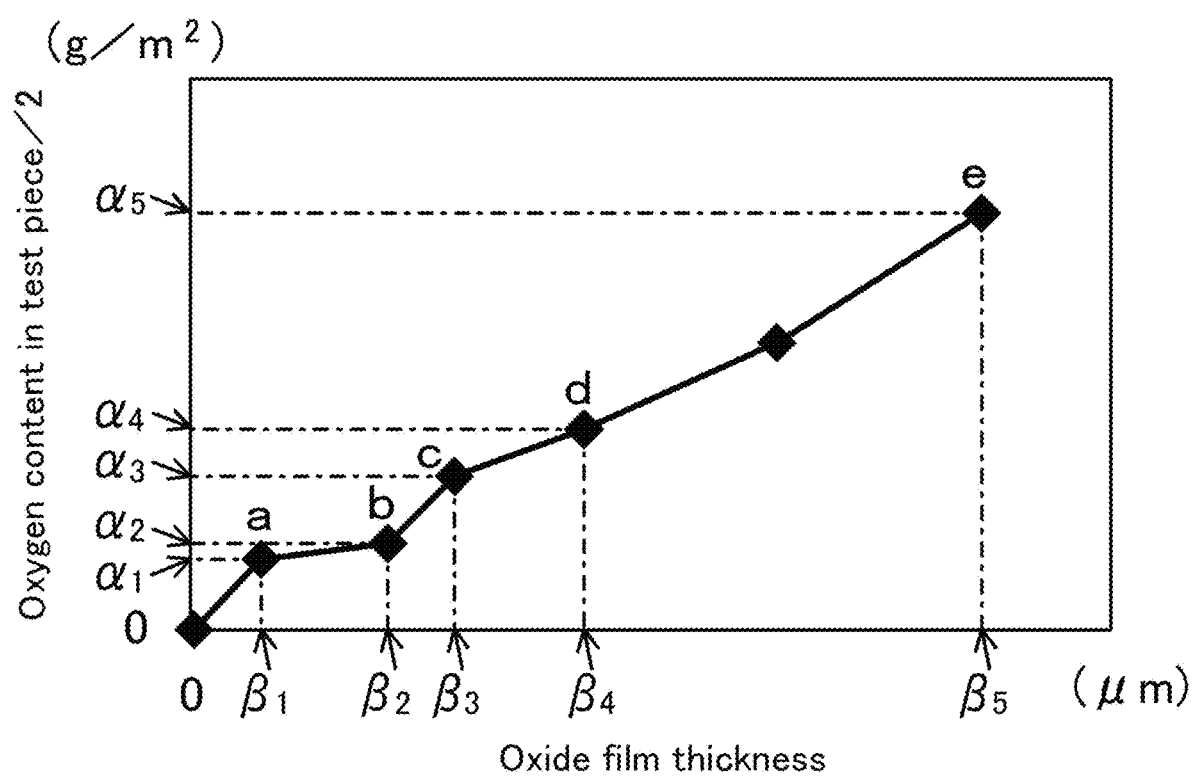
FIG. 3 is a graph showing the relationship between the amount of oxygen, indicated by the vertical axis, and the thickness of the oxide film, indicated by the horizontal axis, in test pieces from steam-treated products (black coated steel sheets).

The third step (S230) evaluates the oxide film thickness based on the oxygen content measured in the second step and the correlation between oxygen content and oxide film thickness in the coating layer of black coated steel sheets (see FIG. 3).

FIG. 3 shows the relationship between oxygen content in one surface of the test pieces, indicated by the vertical axis, and oxide film thickness, indicated by the horizontal axis. The inventors created this graph by plotting based on a test. The oxide film thickness in FIG. 3 indicates the thickness of the oxide film in one surface of the black coated steel sheet. The oxygen content in FIG. 3 indicates the oxygen content in one surface of the black coated steel sheet, obtained by halving the oxygen content measured in the second step.

FIG. 3 shows that oxygen content tends to increase as oxide film thickness increases. In addition, FIG. 3 shows that oxygen content and oxide film thickness are in one-to-one correspondence. Thus, there is a definite correlation between oxygen content and oxide film thickness.

For example, at point a in FIG. 3, the oxygen content $\alpha_1$ (g/m$^2$) corresponds to the oxide film thickness $\beta_1$ (μm) (this is the thickness of the oxide film in one surface of the black coated steel sheet). In the same way, at point b, the oxygen content $\alpha_2$ (g/m$^2$) corresponds to the oxide film thickness $\beta_2$ (μm). At point c, the oxygen content $\alpha_3$ (g/m$^2$) corresponds to the oxide film thickness $\beta_3$ (μm). At point d, the oxygen content $\alpha_4$ (g/m$^2$) corresponds to the oxide film thickness $\alpha_4$ (μm). At point e, the oxygen content $\alpha_5$ (g/m$^2$) corresponds to the oxide film thickness $\beta_5$ (μm).

A bending test of black coated steel sheets can reveal the range of oxide film thickness (the thickness of the oxide film in one surface of a black coated steel sheet) in which the oxide film can be prevented from coming off (and thus scattering powder) during bending. Assuming that this range is $\leq \beta_{TH}$ (μm), and $\beta_{TH}$ (μm) corresponds to an oxygen content of $\alpha_{TH}$ (g/m$^2$), it follows that if the oxygen content measures $\alpha_{TH}$ (g/m$^2$) or less, the oxide film thickness is appropriate.

(Fourth step)

Figure 4:
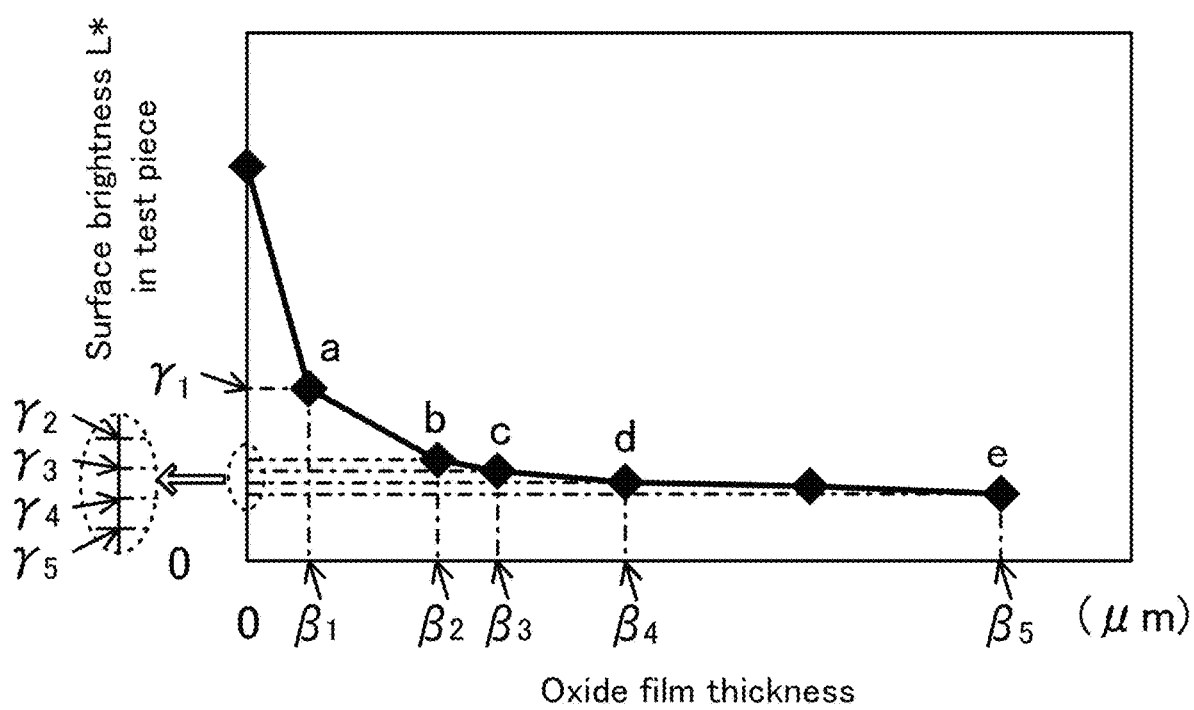
FIG. 4 is a graph showing the relationship between surface brightness, indicated by the vertical axis, and average oxide film thickness, indicated by horizontal axis, in test pieces from steam-treated products (black coated steel sheets).

The fourth step (S240) evaluates the surface brightness based on the oxygen content measured in the second step, the correlation between oxygen content and oxide film thickness (see FIG. 3), and the correlation between surface brightness and oxide film thickness in black coated steel sheets (see FIG. 4).

FIG. 4 shows the relationship between surface brightness, indicated by the vertical axis, and oxide film thickness, indicated by the horizontal axis. The inventors created this graph by plotting based on a test. FIG. 4 shows that surface brightness tends to decrease as oxide film thickness increases. In addition, FIG. 4 shows that surface brightness and oxide film thickness are in one-to-one correspondence. Thus, there is a definite correlation between surface brightness and oxide film thickness. At the same time, there is a definite correlation between oxygen content and oxide film thickness, as described above (see FIG. 3). Therefore, there is a definite correlation between surface brightness and oxygen content.

For example, at point a in FIG. 3, the oxygen content $\alpha_1$ (g/m$^2$) corresponds to the oxide film thickness $\beta_1$ (μm), while at point a in FIG. 4, the oxide film thickness $\beta_1$ (μm) corresponds to the surface brightness $\gamma_1$ (L* value). In the same way, at point b in FIG. 3, the oxygen content $\alpha_2$ (g/m$^2$) corresponds to the oxide film thickness $\beta_2$ (μm), while at point b in FIG. 4, the oxide film thickness $\beta_2$ (μm) corresponds to the surface brightness $\gamma_2$. At point c in FIG. 3, the oxygen content $\alpha_3$ (g/m$^2$) corresponds to the oxide film thickness $\beta_3$ (μm), while at point c in FIG. 4, the oxide film thickness $\beta_3$ (μm) corresponds to the surface brightness $\gamma_3$. At point d in FIG. 3, the oxygen content $\alpha_4$ (g/m$^2$) corresponds to the oxide film thickness $\beta_4$ (μm), while at point d in FIG. 4, the oxide film thickness $\beta_4$ (μm) corresponds to the surface brightness $\gamma_4$. At point e in FIG. 3, the oxygen content $\alpha_5$ (g/m$^2$) corresponds to the oxide film thickness $\beta_5$ (μm), while at point b in FIG. 4, the oxide film thickness $\beta_5$ (μm) corresponds to the surface brightness $\gamma_5$.

An observation of the surface of black coated steel sheets can reveal the range of surface brightness (L*) in which a beautiful black appearance can be realized. Assuming that this range is $\leq \gamma_{IN}$, and $\gamma_{IN}$ corresponds to an oxygen content of $\alpha_{IN}$ (g/m$^2$), it follows that if the oxygen content measures $\alpha_{IN}$ (g/m$^2$) or more, the surface brightness is appropriate.

(Fifth Step)

The fifth step (S250) comprehensively evaluates the quality of the oxide film based on the evaluations in the third and fourth steps.

In the third step, the oxide film thickness is judged as appropriate (that is, accepted) if the oxygen content measures $\alpha_{TH}$ (g/m$^2$) or less. In the fourth step, the surface brightness is judged as appropriate (that is, accepted) if the oxygen content measures $\alpha_{IN}$ (g/m$^2$) or more. Accordingly, the fifth step accepts the quality of the oxide film if the oxygen content is in the range of $\alpha_{IN}$ (g/m$^2$) to $\alpha_{TH}$ (g/m$^2$). This means that the quality of the oxide film, accompanied by appropriate oxide film thickness and appropriate surface brightness, gains comprehensive acceptance. If the oxygen content is less than $\alpha_{IN}$ (g/m$^2$), the oxide film thickness is appropriate, but the surface brightness is inappropriate. In this case, the quality of the oxide film fails to gain comprehensive acceptance. If the oxygen content is more than $\alpha_{TH}$ (g/m$^2$), the surface brightness is appropriate, but the oxide film thickness is inappropriate. Also in this case, the quality of the oxide film fails to gain comprehensive acceptance.

EXAMPLES

Below is a description of an example showing how the present invention works and what effects the present invention has.

This example made five black coated steel sheets with different steam treatment times. These black coated steel sheets had oxide films on both surfaces. Test pieces (100) (see FIG. 2), discs with a diameter of 8 mm, were stamped out from the black coated steel sheets using a punch and a die.

Then the oxygen content ($g/m^2$) in the test pieces (100) was measured using an oxygen amount measuring device (HORIBA EMGA-930). In this measurement, 0.5 g Sn pellets (99% pure) and 0.5 g Ni pellets (99% pure) as metal solvents were put in the oxygen amount measuring device with the test pieces (100).

The measured oxygen content in the five test pieces (100) was examined with the correlations shown in FIGS. 3 and 4 to determine the oxide film thickness and the surface brightness of each test piece (100). This calculation of oxide film thickness and surface brightness was performed by a computer with a program for calculating oxide film thickness and surface brightness based on the correlations shown in FIGS. 3 and 4. FIG. 5 shows the results: the cross-sections of the five test pieces (100) in (a) to (e) with data on oxygen content, oxide film thickness and surface brightness.

The five test pieces (100) were then evaluated based on the acceptance criteria described above. A computer with such a program performed this evaluation. The oxide films in (b), (c) and (d) in FIG. 5 gained comprehensive acceptance (both the oxide film thickness and the surface brightness were appropriate), whereas the oxide film in (a) failed to gain comprehensive acceptance (the oxide film thickness was appropriate, but the surface brightness was inappropriate), and the oxide film in (e) also failed to gain comprehensive acceptance (the surface brightness was appropriate, but the oxide film thickness was inappropriate).

(Discussion)

The five test pieces (100) in (a) to (e) in FIG. 5 were put in the oxygen amount measuring device to measure the amount of oxygen in each, which took only approximately 5 minutes. The measurement results served as the basis for easy and quick calculation of oxide film thickness and surface brightness. The evaluation of oxide film thickness based on the oxygen content in the test pieces (100) is wide-reaching and precise when compared to the conventional evaluation of oxide film thickness, which is merely observing the end faces of the test pieces. The measured oxygen content includes the oxygen content in the substrate steel sheet, but when compared to the oxygen content in the oxide film, the oxygen content in the substrate steel sheet is negligibly low and does not substantially affect the accuracy in measuring the oxygen content in the oxide film.

(Effects)

The method according to the present invention allows easy, quick and precise evaluation of the quality of oxide films in steam-treated products, such as black coated steel sheets.

The above-described embodiment evaluates both oxide film thickness and surface brightness. However, evaluating only oxide film thickness or surface brightness is also possible.

INDUSTRIAL APPLICABILITY

The method according to the present invention allows easy, quick and precise evaluation of the quality of oxide films in steam-treated products such as black coated steel sheets. The evaluation is fed back to the manufacturing process of black coated steel sheets (steam treatment of the coating layer) for quality control. Thus, black coated steel sheets are manufactured with good designability and formability, leading to the increased popularity of black coated steel sheets.

REFERENCE SIGNS LIST

100 Test piece
101 Steel sheet cut-out part
102 Coating layer cut-out part
103 Oxide film

What is claimed is:

1. A method for evaluating the quality of a steam-treated product with at least one oxide film formed during a steam treatment, wherein a thickness of said at least one oxide film and a surface brightness of the steam-treated product are varied corresponding to a time period of the steam treatment, the method comprising steps as follows:

cutting out a test piece from said steam-treated product;

measuring an amount of oxygen in said test piece to get a measured oxygen content; and based on a range of the measured oxygen content in said test piece, evaluating at least the surface brightness of the oxide film of the test piece; or evaluating the surface brightness and the thickness of the oxide film of said test piece.

2. The method for evaluating the quality of steam-treated product according to claim 1, wherein said steam-treated product include a steel sheet and at least one coating layer integrally formed on at least one surface of said steel sheet, and said at least one oxide film is formed on said at least one coating layer;

said test piece include a steel sheet cut-out part that is cut out from said steel sheet, and at least one coating layer cut-out part integrally formed on at least one surface of said steel sheet cut-out part, and said measurement of the amount of oxygen is performed by sending the test pieces integrating said steel sheet cut-out part and said at least one coating layer cut-out part to an oxygen amount measuring device; and using an oxygen amount measuring device to perform said measurement of the amount of oxygen within the test piece integrating said steel sheet cut-out part, said at least one coating layer cut-out part and said oxide film.

* * * * *